(12) United States Patent
Nomoto et al.

(10) Patent No.: US 7,057,744 B2
(45) Date of Patent: Jun. 6, 2006

(54) METHOD AND APPARATUS FOR MEASURING THICKNESS OF THIN FILM AND DEVICE MANUFACTURING METHOD USING SAME

(75) Inventors: Mineo Nomoto, Yokohama (JP); Takenori Hirose, Machida (JP); Keiya Saito, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/082,520

(22) Filed: Feb. 22, 2002

(65) Prior Publication Data
US 2003/0022400 A1    Jan. 30, 2003

(30) Foreign Application Priority Data
Jul. 27, 2001    (JP) ............................. 2001-226984

(51) Int. Cl.
*G01B 11/28* (2006.01)
(52) U.S. Cl. ...................... 356/630; 356/632
(58) Field of Classification Search ........ 356/630–632; 451/6, 5; 438/14, 16
See application file for complete search history.

(56) References Cited

U.S. PATENT DOCUMENTS

| 5,087,121 | A | * | 2/1992 | Kakuchi et al. ............... 356/73 |
| 6,004,187 | A | * | 12/1999 | Nyui et al. ..................... 451/5 |
| 6,159,073 | A | * | 12/2000 | Wiswesser et al. ............ 451/6 |
| 6,271,047 | B1 | * | 8/2001 | Ushio et al. ................... 438/14 |
| 6,425,801 | B1 | * | 7/2002 | Takeishi et al. ................ 451/5 |
| 6,503,361 | B1 | * | 1/2003 | Nyui et al. ............. 156/345.13 |
| 6,551,172 | B1 | * | 4/2003 | Nyui et al. ..................... 451/6 |
| 6,670,200 | B1 | * | 12/2003 | Ushio et al. ................... 438/14 |
| 2002/0197871 | A1 | * | 12/2002 | Hirose et al. ............... 438/689 |

FOREIGN PATENT DOCUMENTS

| JP | 06-252113 | 9/1994 |
| JP | 09-007985 | 1/1997 |
| JP | 10-083977 | 3/1998 |
| JP | 10-294297 | 11/1998 |
| JP | 2000-077371 | 3/2000 |
| JP | 2000-310512 | 11/2000 |

* cited by examiner

*Primary Examiner*—Hoa Q. Pham
(74) *Attorney, Agent, or Firm*—Townsend and Townsend and Crew LLP

(57) ABSTRACT

A method for high-precision measurement of film thickness and the distribution of film thickness of a transparent film is disclosed. The method is performed during a CMP process, without being affected by the film thickness distribution among the LSI regions or on the semiconductor wafer surface. The film thickness is measured by specifying relatively level measurement regions, according to a characteristic quantity of the spectral waveform of the reflected light from the transparent film, such as the reflection intensity, frequency spectrum intensity. This permits highly accurate control of film thickness. The leveling process in CMP processing can be optimized on the basis of the film thickness distribution.

24 Claims, 15 Drawing Sheets

(A) WIRING CIRCUIT
PATTERN SECTION (B) PERIPHERAL CIRCUIT
PATTERN SECTION (a) WIRING CIRCUIT SECTION (b) MEMORY CIRCUIT SECTION (c) PERIPHERAL CIRCUIT SECTION (a)　　　　　　　　　　　(b)

(c)

(a)            (b)

METHOD AND APPARATUS FOR MEASURING THICKNESS OF THIN FILM AND DEVICE MANUFACTURING METHOD USING SAME

BACKGROUND OF THE INVENTION

The present inaction relates to a method for manufacturing semiconductor devices whilst measuring the thickness and thickness distribution of transparent film and controlling the film thickness, for example, a method for measuring uppermost film thickness of a wafer in a surface levelling process stage after film deposition, the levelling process stage in the manufacture of a semiconductor device being controlled by measuring the film thickness. Examples of such transparent films include, in addition to the foregoing, resist films and insulating films, and the like, in manufacturing stages of thin film devices, such as DVD, TFT and LSI reticles, and the like.

For example, semiconductor devices are manufactured by forming devices and wiring patterns onto a silicon wafer, by means of film deposition, exposure and etching processes. In recent years, in order to achieve higher precision and higher density in such devices, there have been moves towards greater fineness and increased layering. This has resulted in an increase in the number of indentations in the wafer surface. Such indentations in the wafer impede the light exposure process, which is essential in forming wiring, and the like, and therefore levelling of the wafer surface is carried out. A CMP (Chemical Mechanical Polishing) technique, wherein the surface of the wafer is levelled by polishing based on chemical and physical actions, is used for this levelling process. CMP is a commonly known technique in the related technological field.

The principal problem involved with CMP processing is that of controlling film thickness. In particular, it is necessary to reduce variation in the high-precision evenness and film thickness of the wafers by incorporating an in-situ measuring system into the CMP system in order to measure the film thickness during the CMP process, and halting the process when the wafer has been processed to a prescribed film thickness. Consequently, a variety of methods have been proposed as in-situ measurement techniques.

Japanese Patent Laid-open No. (Hei)6-252113 and Japanese Patent Laid-open No. (Hei)9-7985 disclose in-situ measuring systems capable of measuring the film thickness over the actual device pattern (at the fine circuit pattern constituting the actual product). In Japanese Patent Laid-open No. (Hei)6-252113, in measuring the film thickness over the actual device pattern, the spectrum of the interference pattern produced by the film from white light is analyzed with respect to frequency, and the absolute value of the thin film is calculated by observing the relationship between the frequency component relating to the spectral waveform and the film thickness. On the other hand, in Japanese Patent Laid-open No. (Hei)10-83977, the change with respect to processing time of the intensity of the interference pattern produced by the transparent film from a laser (single-wavelength source) is detected and the film thickness is calculated from the frequency component relating to that waveform.

Moreover, Japanese Patent Laid-open No. (Hei)10-294297 and Japanese Patent Laid-open No. 2000-77371 disclose techniques for performing in-situ measurement by specifying measurement positions. In Japanese Patent Laid-open No. (Hei)10-294297, the measurement positions are specified by extracting the characteristics of the image of the circuit pattern, or by forming a diffraction pattern in the scribe area of the pattern. In Japanese Patent Laid-open No. 2000-77371, the maxima and minima of the spectral waveform are observed, and measurement points for measuring the film thickness during processing are specified by comparison of these with previously measured maxima and minima of spectral waveforms.

Generally, there have been problems in managing film thickness to a high degree of accuracy by means of the CMP processing time, since the polishing amount (polishing rate) per unit time varies, and the polishing rate also differs according to the ratio of the wafer plane occupied by the pattern formed thereon (hereinafter, called "pattern area ratio"). FIG. 17 shows the film thickness distribution measurement results for a semiconductor device measured using the technique disclosed in Japanese Patent Laid No. 2000-310512. FIG. 17 illustrates film thickness distribution measurement results 160 for a transparent film (insulating film between layers) having an area of approximately 20 mm on a wafer that has been CMP processed. FIG. 17 shows the film thickness distribution in the wiring pattern sections 161, 162, peripheral circuit section 163, and the border section 164, 165 between the peripheral circuit section and the wiring pattern sections. As these film thickness distribution measurement results 160 show, a film thickness change of several 100 nm occurs in a region of approximately 2 mm at the border sections 164, 165 between the peripheral circuit sections and the wiring pattern sections. On the other hand, the wiring patterns sections 161, 162 and the peripheral circuit section 163 themselves has a comparatively even film thickness over regions of several mm.

This film thickness distribution is produced by the pattern area ratio, and processing conditions such as the type of polishing pad in the processing device, the type of polishing fluid (slurry), and the like, and it may vary between products or between each wafer, due to variations in the type of semiconductor or circuit pattern, and in the processing conditions (state of wear of the polishing pad, density of slurry, and the like). As described above, in in-situ measurement during the CMP process, a problem arises in that, depending of the observed field being measured, the measurement accuracy declines as regions having great variation in film thickness are measured. Furthermore, although Japanese Patent Laid-open No. (Hei)10-294297 and Japanese Patent Laid-open No. 2000-77371 disclose methods for specifying measurement points, even in these disclosures, no particular attention is given to the measurement fields, which are specified over a relatively large region (diameter of approximately 2 mm), and hence there is a risk that measurement accuracy will decline when the film thickness is measured in a state such as that illustrated in FIG. 17.

In other words, the spectral waveform provides waveform data including information from a broad area of varying film thickness and underside wiring state, and hence it is difficult to specify the desired measurement points. Therefore, it is not possible to reduce fluctuation in high-precision evenness and film thickness characteristics by terminating the CMP processing at the moment that the wafer has been processed to a prescribed film thickness, thereby making it difficult to control film thickness to a high degree of accuracy and hence leading to a decline in semiconductor device yield. Moreover, conventionally, slurry has been used as a polishing fluid in CMP processing.

As also disclosed in Japanese Patent Laid-open No. (Hei)10-83977, in-situ measurement is conducted by forming a transparent window in the polishing band and extracting the spectral waveform from the wafer surface in the slurry. Since the slurry is a polishing fluid containing particles of silica, potassium hydroxide, and the like, it is optically semi-transparent, and has poor light transmission characteristics. Furthermore, the spectral reflectivity of the wafer surface is also reduced markedly by the occurrence of glass-type indentations in the transparent window due to the action of the particles contained in the polishing fluid, and hence the spectrum cannot be measured in a stable fashion, thereby making it difficult to achieve high-precision control of the film thickness by terminating CMP processing at the moment that the wafer has been processing to a prescribed film thickness.

SUMMARY OF THE INVENTION

The present invention provides a method and device whereby the film thickness of a transparent film can be measured to a high degree of accuracy during a CMP process, without being affected by the film thickness distribution in the LSI region arising in the CMP process, and a manufacturing method and manufacturing device for thin film devices using same.

Moreover, the present invention provides a method and device whereby the film thickness of a transparent film can be measured to a high degree of accuracy during a CMP process, without being affected by the film thickness distribution within the wafer surface arising in the CMP process, and a manufacturing method and manufacturing device for thin film devices using same.

Furthermore, the present invention provides a method and device whereby the film thickness of a transparent film can be measured to a high degree of accuracy and in a desired measurement field during a CMP process, without being affected by the film thickness distribution in the LSI region or the film thickness distribution in the wafer surface arising in the CMP process, and a manufacturing method and manufacturing device for thin film devices using same.

Furthermore, the present invention provides a method and device whereby the film thickness of a transparent film can be measured to a high degree of accuracy by specifying desired measurement positions, during a CMP process, without being affected by the film thickness distribution in the LSI region or the film thickness distribution in the wafer surface arising in the CMP process, and a manufacturing method and manufacturing device for thin film devices using same.

Furthermore, the present invention provides a method and device hereby the film thickness of a transparent film can be measured to a high degree of accuracy by specifying desired measurement positions and a desired measurement field, during a CMP process, without being affected by the film thickness distribution in the LSI region or the film thickness distribution in the wafer surface arising in the CMP process, and the film thickness measurement results thereof are used in processing conditions for manufacturing processes after the CMP processing stage (etching, film deposition, and the like), and a manufacturing method and manufacturing device for thin film devices using same.

Furthermore, the present invention provides a method and device whereby the film thickness of a transparent film can be measured to a high degree of accuracy by extracting a spectral waveform having a high S/N ratio, during a CMP process, without being affected by reduction in the spectral transmission characteristics of the slurry arising during CMP processing, and a manufacturing method and manufacturing device for thin film devices using same.

Furthermore, the present invention provides a method and device whereby the film thickness of a transparent film can be measured to an accuracy of several 10 nm or less over the actual device pattern, for example, during a CMP process, without being affected by the film thickness distribution in the LSI region arising in the CMP process, and a manufacturing method and manufacturing device for thin film devices using same. In other words, the present invention provides a method and device capable of high-precision control of film thickness, and a method and device for achieving improved process throughput, wherein the film thickness of the uppermost surface over the actual device pattern after CMP processing is measured by using a measurement technique such as that disclosed in the Japanese Patent Laid-open No. 2000-310512, the film thickness distribution in the LSI region is extracted, a measurement field and measurement positions are determined on the basis of this film thickness distribution result, the spectral waveform is extracted from the desired measurement field and measurement positions of the pattern during CMP processing, and the film thickness of the uppermost surface during CMP processing is measured to a high degree of accuracy.

In the present invention, the field and measurement positions for measuring the film thickness of the transparent film during CMP processing are determined on the basis of the measurement results for film thickness distribution in the LSI region of the actual device pattern having been CMP processed. The technique for measuring the actual device pattern is such that the film thickness distribution of the device pattern is measured using a film thickness measuring method (hereinafter, called actual pattern film thickness measuring method) such as that disclosed in Japanese Patent Laid-open No. 2000-310512 claimed by the present inventors, and a desired measurement field is determined on the basis of these measurement results.

From the example of measurement results in FIG. 17, taking the measurement field as approximately 50–100 μm diameter, desirably, a field of view is adopted which ensures a high measurement precision, even if the film thickness changes suddenly (change of several 100 nm in thickness in approximately 1 mm).

Moreover, if the film thickness distribution is flat in the LSI region, then a larger measurement field of several mm can be adopted.

Desirably, the measurement positions are selected such that the film thickness in relatively flat regions 161, 162 as indicated in FIG. 17 can be measured to a high degree of accuracy. The regions 161 and 162 are wiring circuit pattern sections, and since they are stable and have a wring pattern density below the transparent film of several 10% approximately, then these regions have good evenness during CMP processing. Moreover, in a semiconductor manufacturing process, there are wiring regions where inter-layer connections are made by forming contact holes, or the like, and desirably, the film thickness of these wiring circuit regions is controlled in order to determine etching conditions, and the like, also. The measurement positions determining method according to the present invention is carried out by using one or more of the following means:

(1) extracting the intensity difference in the spectrum of the reflected light;

(2) extracting the frequency spectrum intensity in the spectrum of the reflected light; and (3) comparing with spectral waveforms measured by an actual pattern film thickness measurement method.

According to the present invention, it is possible to control the film thickness in respective positions, by selecting measurement positions from a characteristic quantity of the spectral wavelength from locations such as the LSI peripheral circuit section, scribe area, or the like, and not only the wiring regions.

The foregoing description relates to determining the measurement field and measurement positions in the LSI region (chip region) formed on a semiconductor wafer, but it is also possible to perform film thickness control in the wafer surface. CMP processing is implemented whilst the wafer performs a rotating movement and sliding movement.

In the present invention, the orientation flat position and notch position in the wafer are held in an approximately registered fashion in the wafer holder, the measurement position of the in-situ film thickness measurement system during CMP is judged to be either in the central portion or the peripheral portion of the wafer, on the basis of the orientation flat position and the notch position of the wafer from the wafer holder, and measurement is made and a measurement result output.

Moreover, in the present invention, in order to measure the spectral wave form of the wafer surface at a high S/N ratio, via optically transparent slurry, the slurry can be diluted by supplying optically transparent fluid, such as pure water, or the like, in the vicinity of the spectral waveform measurement waveform. Moreover, by using a material having a refraction index proximate to that of the slurry as the material of the transparent window used for spectral waveform measurement, the increase in reflectivity (increase in spectral transmissivity) due to the difference in refraction index at the border between the slurry and transparent window can be reduced. Therefore, the precision of the film thickness control can be improved by extracting a spectral waveform of high S/N ratio even during CMP processing.

These and other objects, features and advantages of the invention will be apparent from the following more particular description of preferred embodiments of the invention, as illustrated in the accompanying drawings.

DESCRIPTION OF THE PREFERRED EMBODIMENTS

An embodiment of the present invention is now described, being an example wherein a method for measuring the thickness of transparent film formed on a wafer surface to an accuracy of several 10 nm or less over the actual device pattern, for example, is applied with respect to a CMP processing stage in the manufacture of a semiconductor.

Figure 1:
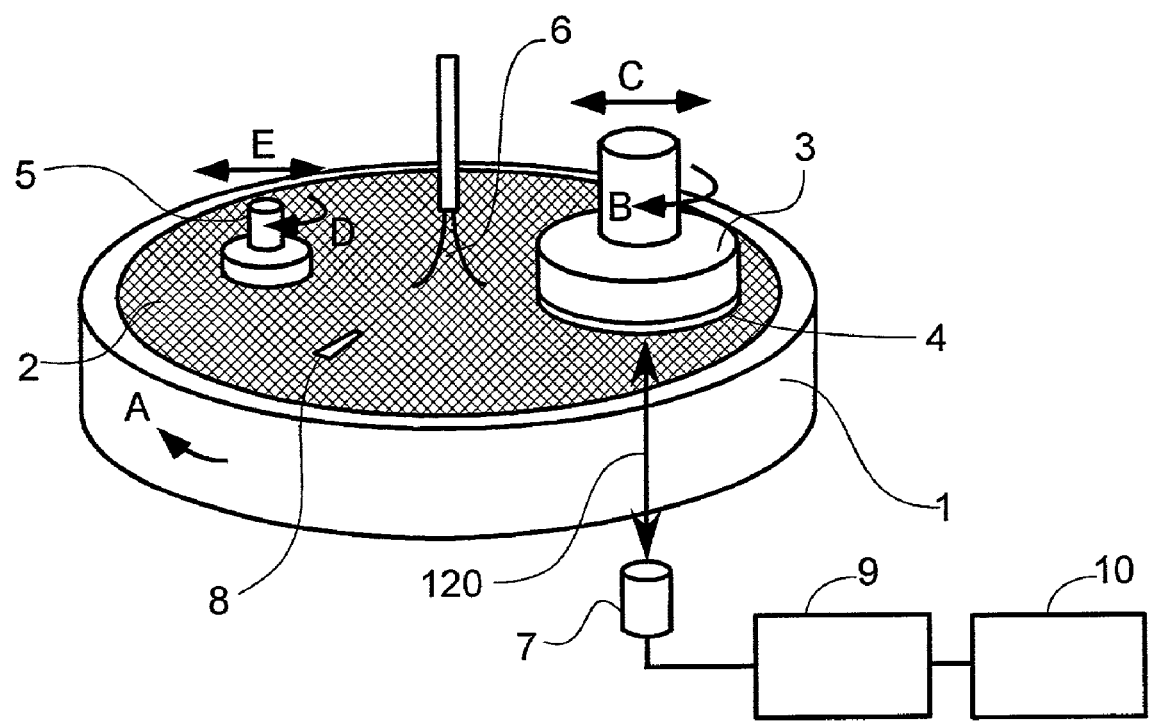
FIG. 1 is a perspective view showing the general composition of a CMP polishing device provided with film thickness measuring means according to the present invention.

FIG. 1 shows one embodiment wherein the film thickness control method according to the present invention is applied to a CMP device. The CMP device comprises a polishing pad 2 formed on a polishing base 1, the wafer 4 to be processed being held in a holder 3. Furthermore, the pad is periodically dressed by a dresser 5 disposed above the polishing pad 2 which dresses the pad surface in such a maser that a uniform processing rate is maintained. A structure is formed for supplying a liquid slurry 6 containing polishing granules onto the polishing pad. In order to measure the film thickness during CMP processing, a composition is adopted whereby a measurement optics system 7 is able to measure the spectral waveform of the wafer surface from below the polishing base 1, by means of a measurement window 8 provided in the polishing pad 2. A film thickness measurement controller 9 calculates the film thickness from the measured spectral waveform. This film thickness measurement controller 9 is connected to an actual pattern film thickness measuring device 10, in such a manner that it can obtain information from the actual pattern film thickness measuring device 10. This actual pattern film thickness measuring device 10 is a measuring system such as that disclosed in Japanese Patent Laid-open No. 2000-310512, whereby the film thickness distribution for processed wafers of a similar type to the wafer 4 is previously measured, and based on these film thickness distribution measurement results, a measurement conditions controller 11 selects the measurement fields to be used by the measurement optics system 7 and spectral waveforms corresponding to the film thickness at each respective measurement position, and inputs same to the film thickness measurement controller 9.

The whole surface of the wafer 4 is polished by rotating the polishing base 1 in the direction of arrow A, whilst the holder 3 is caused to perform a rotational movement as indicated by arrow B and a sliding movement as indicated by arrow C, and the dresser 5 periodically dresses the pad 2 by performing rotational movement as indicated by arrow D and sliding movement as indicated by arrow E. In the aforementioned composition, as the polishing base 1 rotates, a window glass 81 incorporated into the measurement window 8 passes through the measurement light path 120 of the measurement optics system 7 once for each revolution of the polishing base 1, the spectral waveform of the wafer 4 is detected by the measurement optics system 7, and the detected spectral waveform is input to the film thickness measurement controller 9 which calculates the film thickness at prescribed measurement positions.

Figure 2:
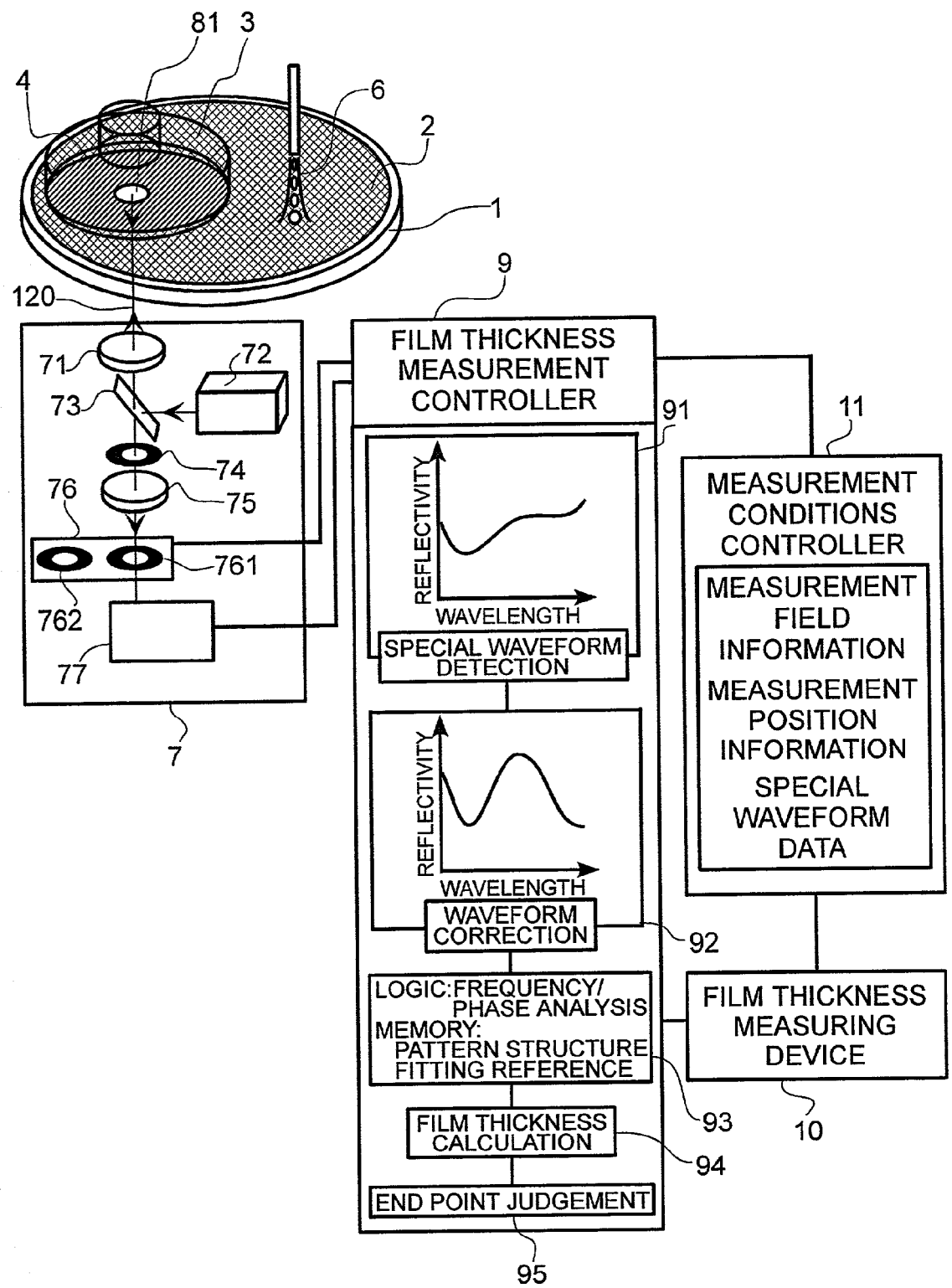
FIG. 2 is a perspective view showing a specific example of a CMP polishing device composition provided with film thickness measuring means according to the present invention.

FIG. 2 shows detailed examples of the measurement optics system 7 and the film thickness measurement controller 9 in FIG. 1. The measurement optics system 7 comprises: a detecting lens 71, illuminating light source 72, half mirror 73, spatial filter 74, focusing lens 75, field of view aperture unit 76, field aperture 761, field aperture 762, and beam splitter 77. In this measurement optics system 7, white illumination light (wavelength 300 nm–800 nm approx.) is irradiated from the illuminating light source, through the half-mirror 73, the detecting lens 71 and the window glass 81, and onto the wafer 4 being processed. The light reflected back by the wafer 4 passes through the spatial filer 74, focusing lens 75, and field aperture 761, to the beam splitter 77, where it is split. The split wavelength signal is measured by the film thickness measurement controller 9, which performs wavelength correction processing 92 for removing the effects of wavelength distortion due to the slurry (described hereinafter), from the resulting spectral waveform 91. A film thickness calculation 94 for the film over the device pattern during processing is performed from the spectral waveform thus corrected, by means of a frequency/phase analysis measurement method or pattern structure fitting measurement method, as disclosed in Japanese Patent Laid-open No. 2000-310512, and processing is terminated at the moment that the wafer has been processed to a prescribed film thickness. Furthermore, the measurement conditions controller 11 inputs measurement field information and spectral waveform data based on the film thickness distribution supplied by the actual pattern film thickness measuring device 10, to the film thickness controller 9.

The film thickness controller 9 judges whether or not the detected spectral waveform 91 is applicable as film thickness measurement data, selects a spectral waveform required for measurement, and uses same to calculate the film thickness. The measurement field is set as a parameter prior to the start of film thickness measurement, and the prescribed measurement field is set by switching the aperture unit 76 of the measurement optics system 7 to determine the field aperture diameter. The spatial filter 74 of the measurement optics system 7 is able to remove diffraction harmonics caused by the light scattered at the edges of the wiring patterns, and the N.A of the detecting lens, and hence wavelength distortion, such as significant distortion of the spectral waveform due to diffracted light, is reduced, thereby improving the S/N characteristics of the spectral waveform.

Figure 3:
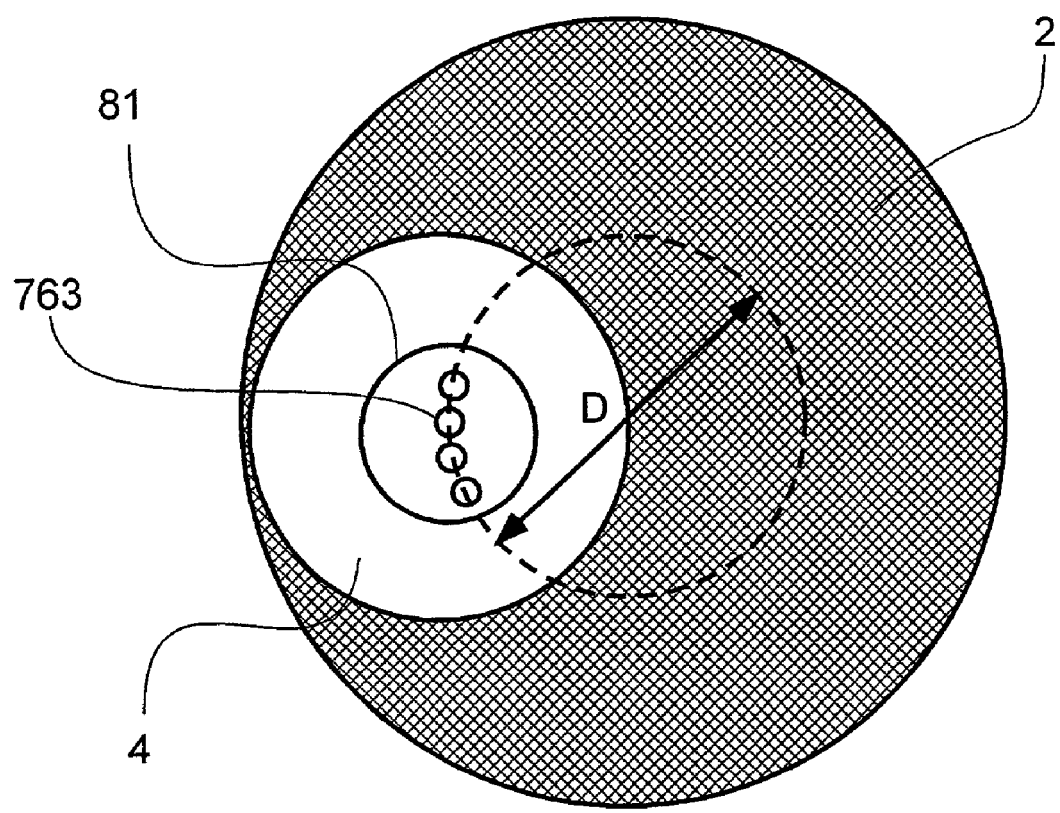
FIG. 3 is a plan view of a polishing pad placed on a wafer, in order to describe a measurement field according to the present invention.

FIG. 3 is a diagram for describing a measurement field in the present embodiment. This conceptual diagram illustrates an example wherein the window glass 81 shown in FIG. 3 is 10–50 mm in size, and the detection field of the measurement field of view 763 is 50–100 μm in diameter, the magnification factor of the optics system being taken into account when determining the field of view size for measuring the spectral waveform. In one revolution of the polishing base 1, the spectral waveform data for a plurality of locations on the wafer 4 is obtained via the window glass 81. In the embodiment in FIG. 3, a state is depicted where spectral data is detected four times, but the higher the number of measurement points, the greater the ability to perform high-precision film thickness evaluation. In practice, the number of measurement samples is determined according to the number of revolutions of the polishing base 1 of the CMP device, the size of the measurement window, the sampling rate of the spectral analyser, the quantity of light produced by the illumination system, the amount of light reflected by the wafer, and the like. In the example shown in FIG. 3, taking the diameter of the polishing base 1 as D$\phi$=250 mm, the number of revolutions as 100 rpm, and the sampling rate of the spectral analyser 77 as 1 mm/s, an area of $\phi$=50 μm×0.4 mm width is measured. If the window glass 81 has a diameter of 10 mm, then 10 measurements can be made. In other words, the required spectral waveform is selected from the spectral data for 10 locations on the wafer 4 during one revolution of the polishing base 1, and these waveforms are input to the film thickness controller 9, which calculates the corresponding film thicknesses.

Next, the present invention is described in concrete terms by reference to FIG. 4–FIG. 7.

Figure 4:
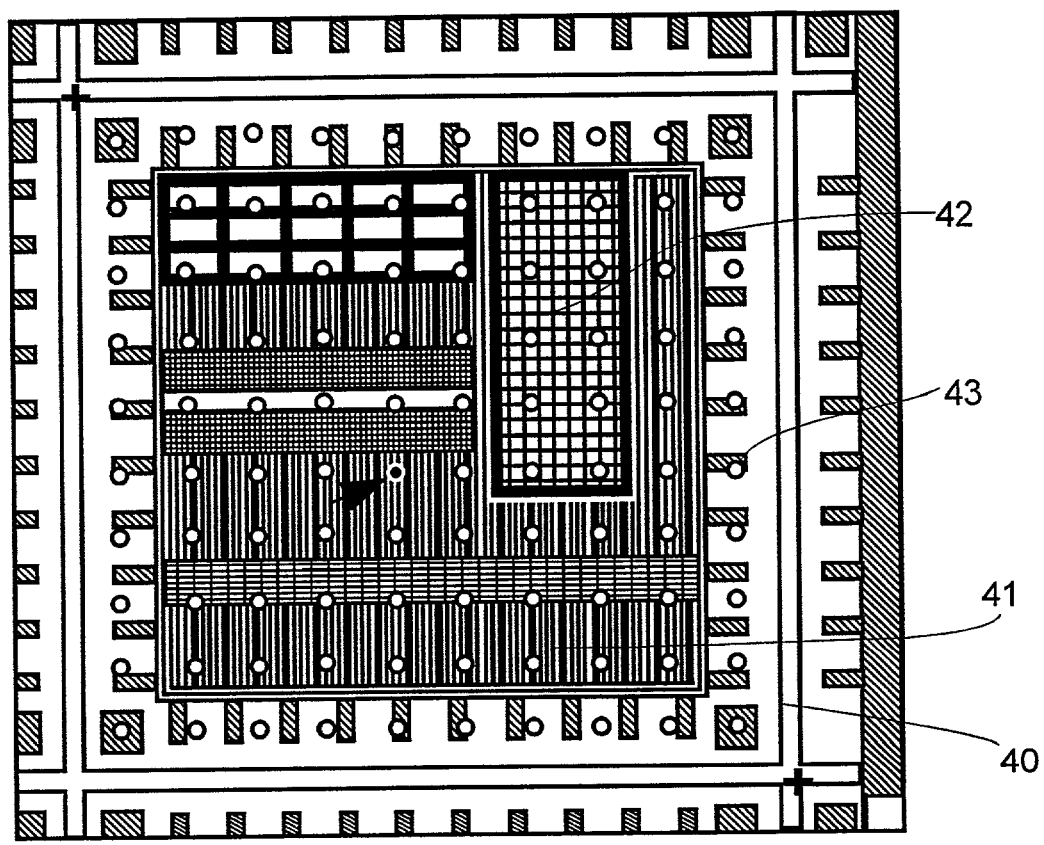
FIG. 4 is a plan view of a semiconductor LSI circuit pattern.
Figure 5:
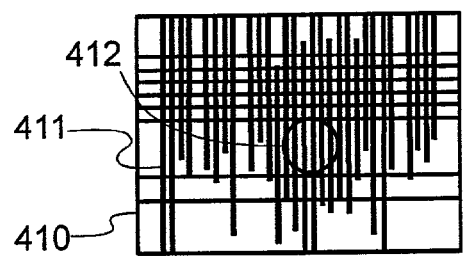
FIG. 5 is a plan view of a semiconductor LSI circuit pattern showing one detailed example of a semiconductor LSI circuit pattern and a measurement field.
Figure 5:
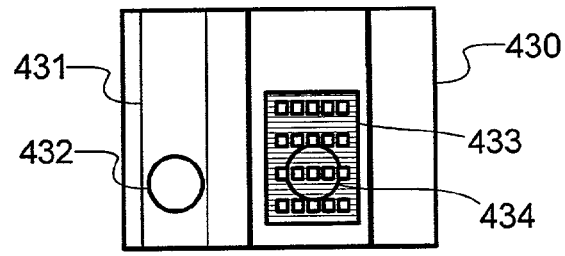

FIG. 4 is one example of an LSI circuit (one chip). A wiring circuit pattern section 41 is formed in the central region of the LSI circuit 40, a portion of the circuit is formed with a memory circuit section 42 having a regulation wiring pattern, and a peripheral circuit pattern section 43 is formed about the periphery of the wiring circuit pattern section 41. FIG. 5 is a partial enlarged view of FIG. 4, illustrating the relationships between the respective wiring sections and the field of view, in a case where a measurement field of 100 μm diameter is used. FIG. 5(a) shows a wiring circuit pattern section 410, and FIG. 5(b) shows a peripheral circuit pattern section 430.

In the most recent LSIs, the wiring pattern 411 is formed to a width of several μm-0.1 μm, and taking the measurement field 412 as having a 100 μm diameter, the surface ratio of the measurement field 412 that is occupied by the pattern will be several 10%. On the other hand, the peripheral circuit patterns 431, 433, are formed to a width of several 10 μm-several 100 μm, and therefore, taking the measurement field 432 as having a 100 μm diameter, t he surface ratio occupied by the pattern in the measurement field 432 will be 50–%100%.

Figure 6:
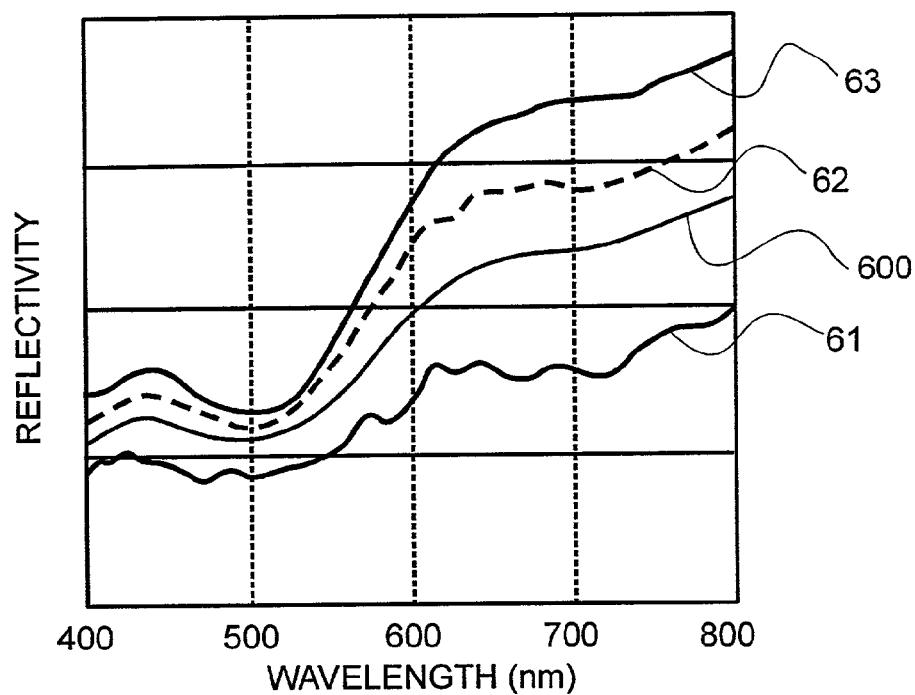
FIG. 6 is a graph showing one example of spectral reflection characteristics from a circuit pattern according to the present invention.

FIG. 6 shows spectral reflection characteristics for the measurement field regions illustrated in FIG. 5. The spectral waveform 61 is a waveform measured using measurement field 412 in FIG. 5, spectral waveform 62, using the measurement field 434 in FIG. 5, and spectral waveform 63, using the measurement field 432 in FIG. 5.

Figure 7:
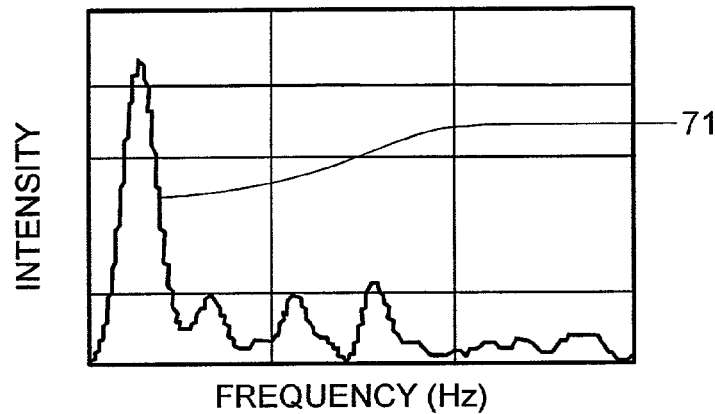
FIG. 7 is a graph showing one example of spectral intensity characteristics from a circuit pattern according to the present invention.
Figure 7:
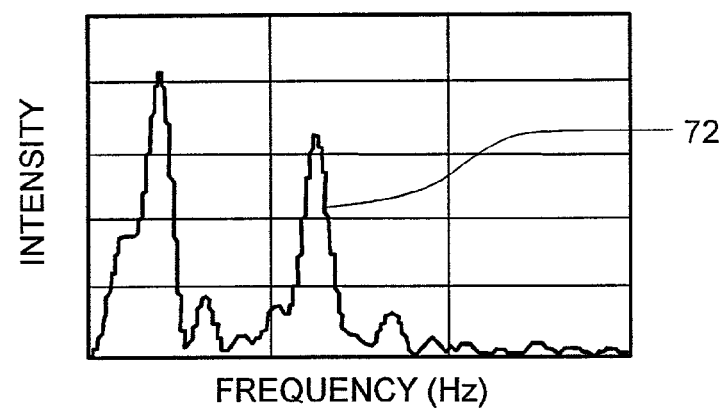
Figure 7:
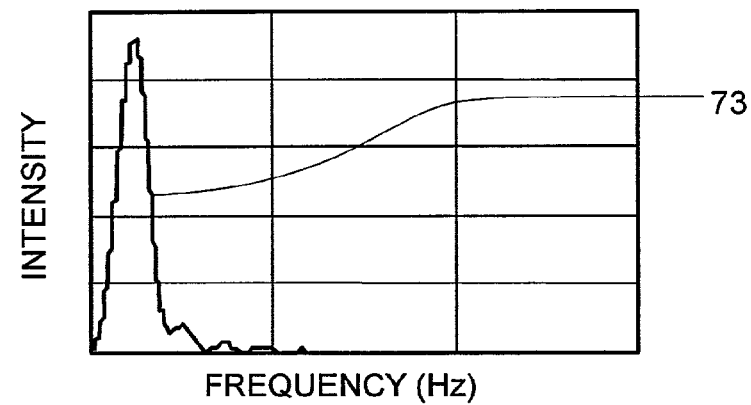

FIG. 7 shows the frequency spectral characteristics for the measurement field regions illustrated in FIG. 5. Specifically, it can be seen that the spectral reflection characteristics vary according to the area ratio of the lower pattern section in the measurement field. If the area ratio occupied by the lower pattern in the measurement field is high, then the spectral reflectivity is high, whereas if this surface area is low, then the reflectivity is low. This tendency is particularly marked in the longer wavelength region. FIG. 7 also shows the frequency spectral characteristics for the measurement field regions illustrated in FIG. 4. FIG. 7(a) shows frequency spectrum characteristics for a wiring circuit section, FIG. 7(b) shows similar characteristics for a memory circuit section, and FIG. 7(c) shows similar characteristics for a peripheral circuit section. It can be seen that, since the spectral characteristics vary according to the form of the wiring pattern occupying the measurement field, the measurement positions can be specified from the frequency spectrum of the spectral waveform.

Moreover, since the characteristics of the spectral waveforms shown in FIG. 6 and FIG. 7 are reproducible for respective wiring sections, it is possible to specify measurement positions by comparing and evaluating similar spectral waveforms and reflectivity, or frequency spectrum characteristics, or the like, on the basis of the spectral waveform data from the actual pattern film thickness measuring device 10 illustrated in FIG. 2.

Figure 8:
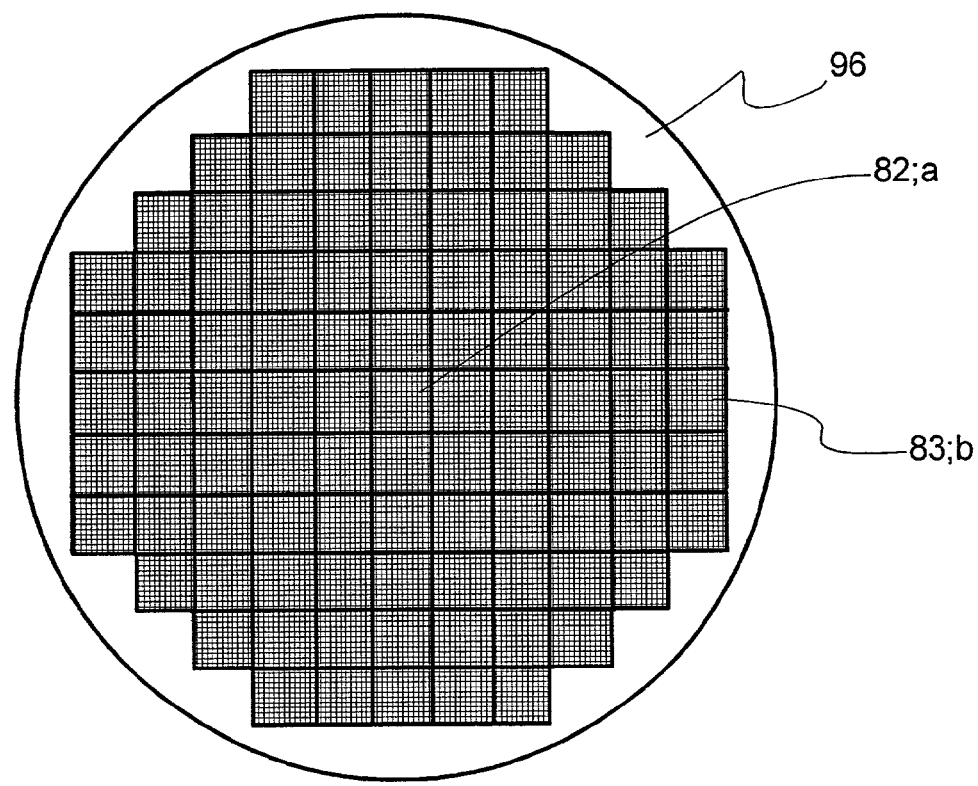
FIG. 8 is a plan view of a semiconductor LSI wafer.
Figure 9:
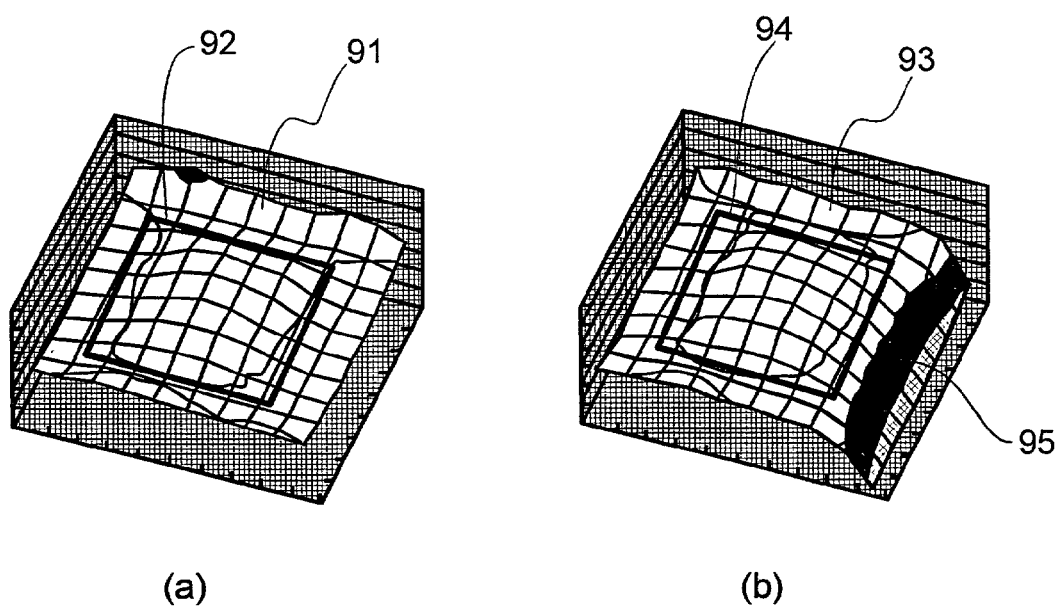
FIG. 9 is a perspective view showing one example of the thickness distribution of a transparent film in a semiconductor LSI.

FIG. 8 is a schematic diagram of a semiconductor wafer. FIG. 9 shows one example of film thickness distribution measurement results as obtained by the actual pattern film thickness measuring device 10 measuring the film thickness in a central chip 82 and peripheral chip 83 in FIG. 8. The measurement results for the centre chip in FIG. 8 indicate that the film in the centre region is slightly thicker and that in the peripheral region is slightly thinner. In FIG. 9(a), the whole ship is flat compared to (b). In FIG. 9(b), the outermost periphery 95 of the chip has a notably thinner film thickness. On the outermost border 96 of the chips, no pattern is formed, and it is thought that here the CMP processing rate will be greatly, and hence the film will be thinner.

Figure 16:
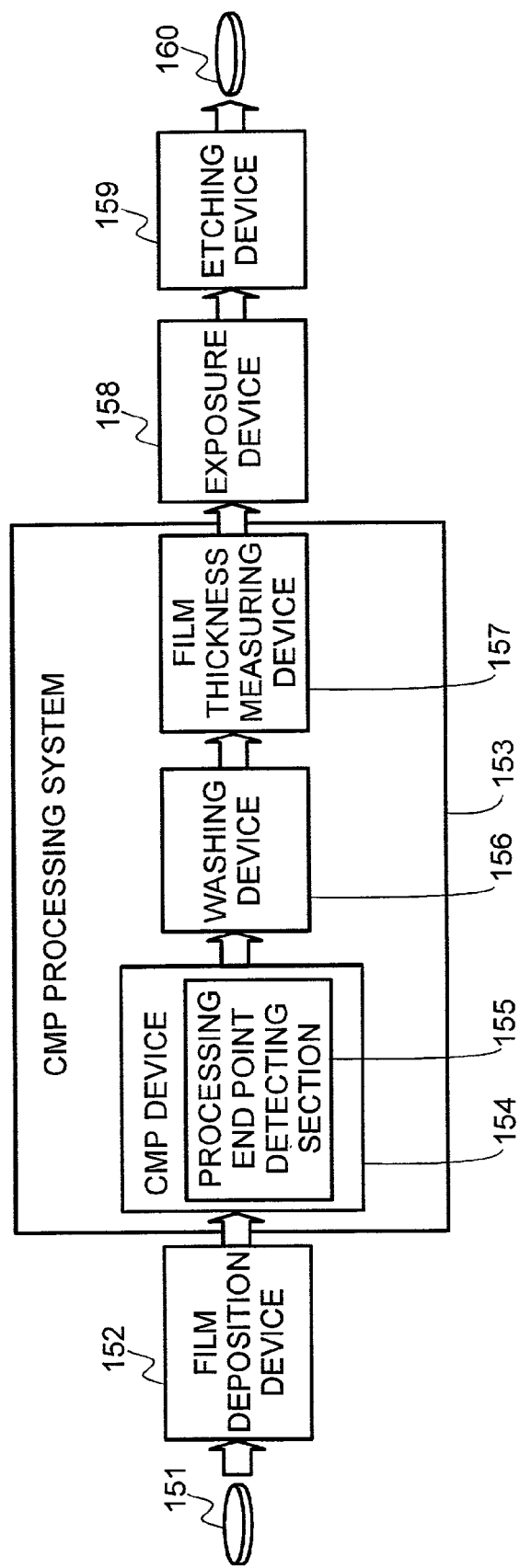
FIG. 16 is a process diagram showing one example of processing stages for manufacturing a semiconductor device using a CMP processing system according to the present invention.
Figure 17:
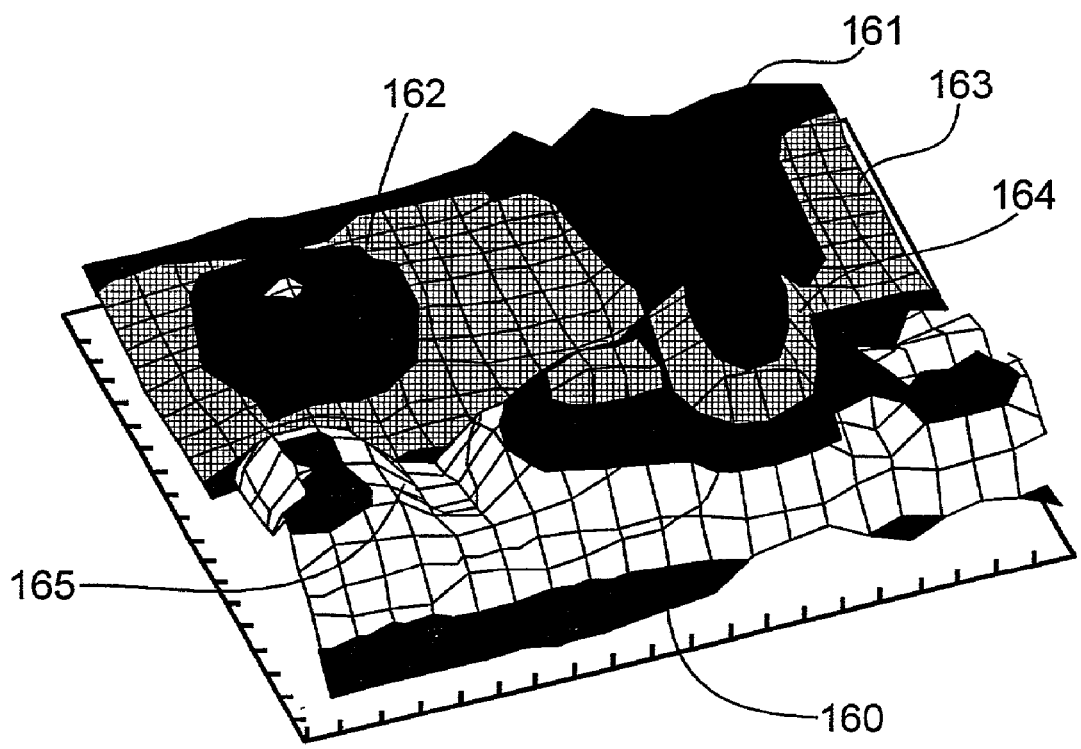
FIG. 17 is a perspective view of a semiconductor LSI showing one example of film thickness distribution of a transparent film in a semiconductor LSI.

In the examples illustrated in FIG. 8, the state of film thickness in the whole wafer can be controlled to a high degree of precision by setting the approximate central regions 92, 93 of the chips as the measurement positions during CMP processing. In other words, higher-precision film thickness control for the whole surface of the wafer can be achieved by identifying a wiring circuit pattern section 412 which can readily be processed to a relatively level state, as illustrated in FIG. 5, for measuring the film thickness in each chip of the wafer surface. According to the present invention, the film thickness distribution within the wafer surface can be measured by specifying either relatively even wiring circuit sections or peripheral circuit pattern sections, rather than the border regions between peripheral circuit pattern sections and wiring circuit pattern sections as illustrated in FIG. 16, or the outer circuit sections, which both display large variation in film thickness.

The spectral waveform in FIG. 6 includes the slurry 6, and therefore is a distorted waveform rather than an ideal sinusoidal waveform. The distortion of the waveform is thought to arise because the reflection intensity from the lower pattern below the transparent film is affected by the fact that the difference in refraction index between the transparent film on the pattern and the slurry is less than that between the transparent film and the air, or the like. In FIG. 6, curve 600 indicates the central trend of the waveform distortion.

Figure 11:
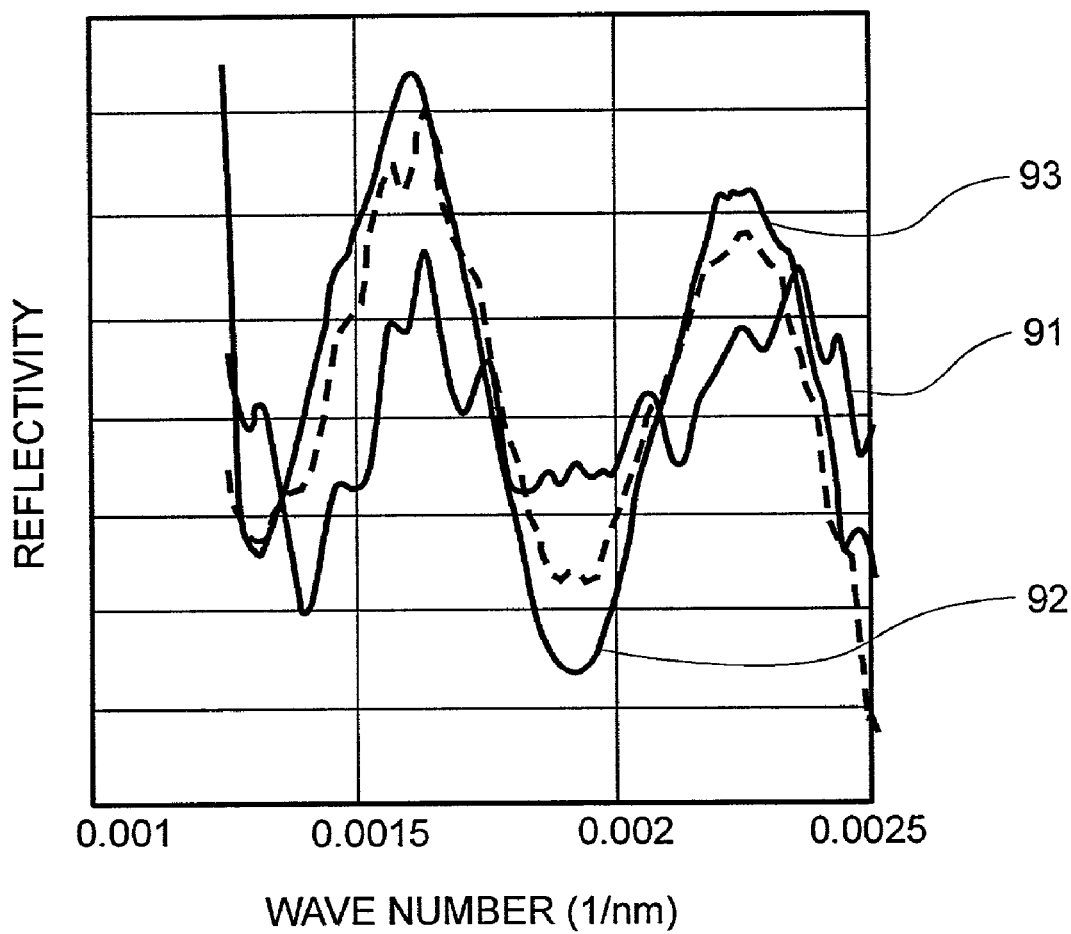
FIG. 11 is a graph showing spectral reflection characteristics for calculating film thickness according to the present invention.

FIG. 11 shows corrected waveform extracted from the respective waveform envelopes by adding and multiplying the central component, which forms a waveform distortion coefficient, with respect to the spectral waveform in FIG. 6, in order to eliminate the trend of the spectral waveform in FIG. 6. In FIG. 11, the spectral waveform 91 corresponds to the spectral waveform 61 in FIG. 6, spectral waveform 92 corresponds to spectral waveform 62 in FIG. 6, and spectral waveform 93 correspond to spectral waveform 63 in FIG. 6. To remove the waveform trend, a method such as that disclosed in Japanese Patent Laid-open No. 2000-310512 may be used, thereby enabling the film thickness to be calculated with high precision by calculating the film thickness from corrected spectral waveforms.

Figure 10:
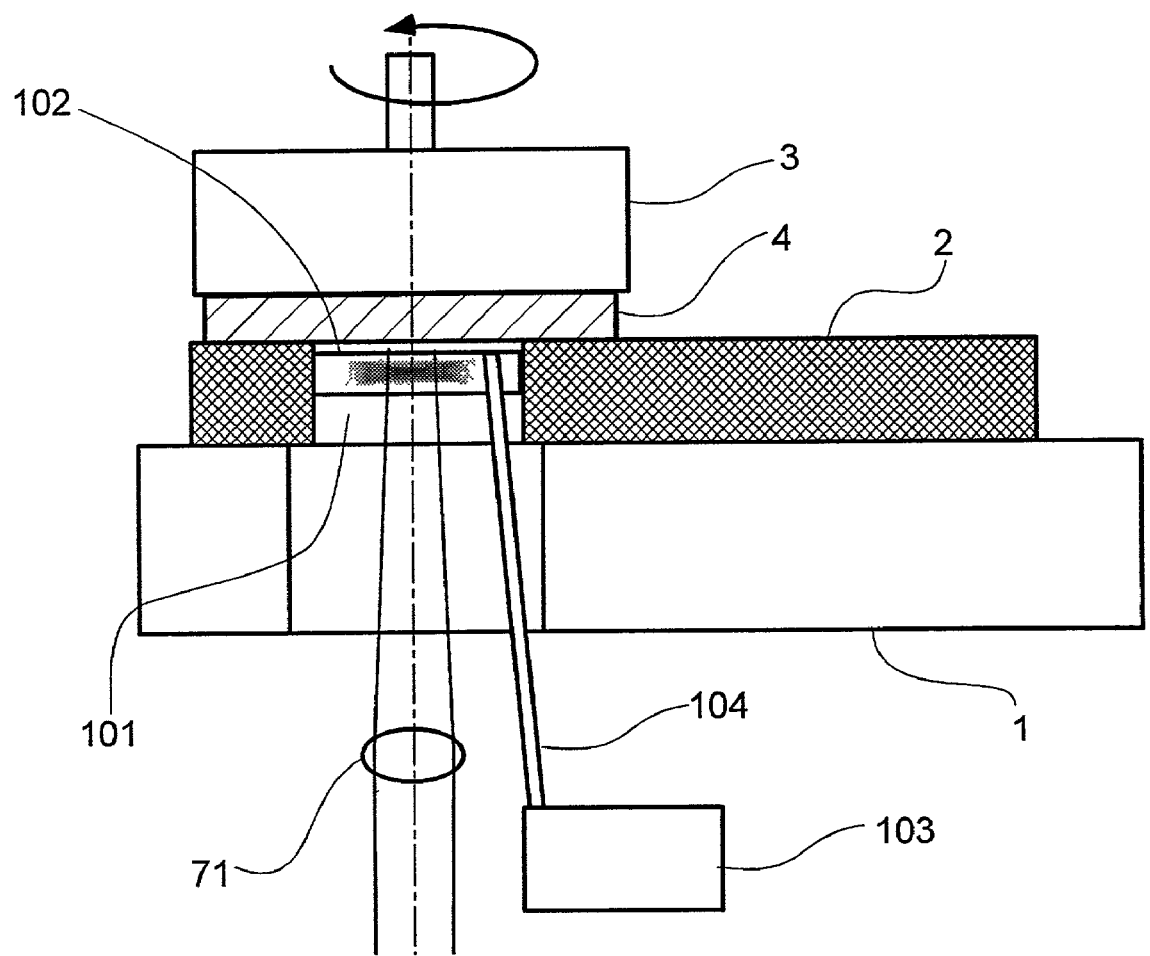
FIG. 10 is a front view showing one example of the structure of a detection window according to the present invention.

FIG. 10 is an explanatory diagram for measuring the spectral waveform of the wafer surface at a high S/N ratio.

In FIG. 10, a window glass 101 having optical characteristics similar to the refraction index of the slurry, for example, a window made of lithium fluoride ($LiF_2$) or magnesium fluoride ($MgF_2$) having a refraction index of approximately 1.4, was used for the window glass 81 in the embodiment of FIG. 2. Since the window glass 101 and the slurry 102 have roughly the same refraction index, the reflection component at the border between these respective elements is reduced, and hence the intensity of reflected light received by the beam splitter 77 increases, thereby improving the S/N ratio of the reflected light after splitting. Moreover, by supplying pure water locally to the slurry 102 in the vicinity of the window glass 101, from a pure water tank 103 via a pipe 104, the slurry 102 is diluted locally, and the slurry solution containing white suspension, such as ground material, and the like, becomes optically transparent. By detecting the reflected light from the wafer surface via this optically transparent water solution, the reflectivity of the spectral waveform shown in FIG. 6 is increased, and furthermore, waveform distortion due to scattering by ground particles in the slurry, and the like, is reduced, resulting in a spectral waveform more proximate to a sinusoidal wave, and hence improving the accuracy of film thickness calculation. The liquid supplied is not limited to being water, provided that it is a liquid which makes the slurry become optically transparent.

Figure 12:
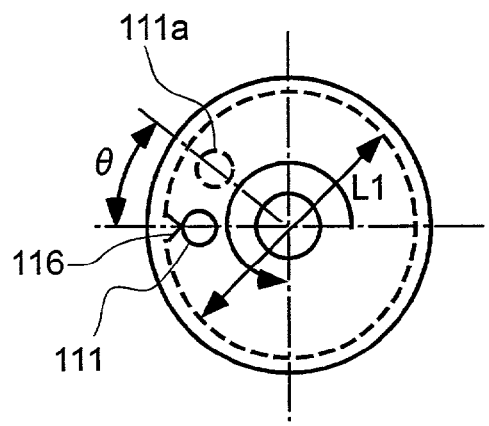
FIG. 12(a) is a front view of a CMP processing device provided with a film thickness measuring function according to the present invention.
FIG. 12(b) is a front view of a CMP processing device according to the present invention.
FIG. 12(c) is a plan view of a holder for a CMP processing device.
Figure 12:
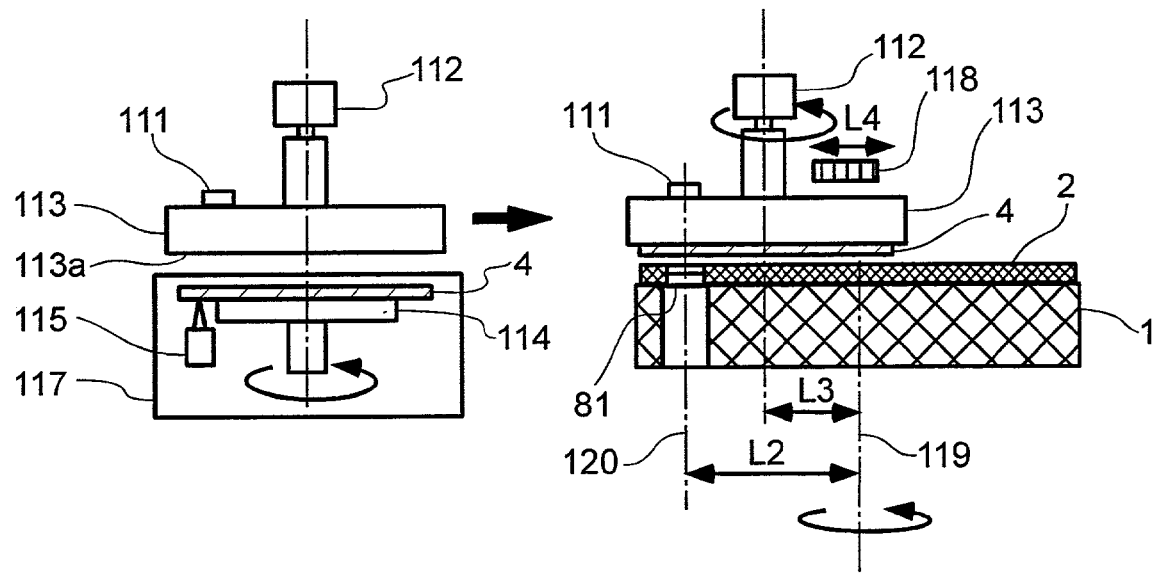
Figure 13:
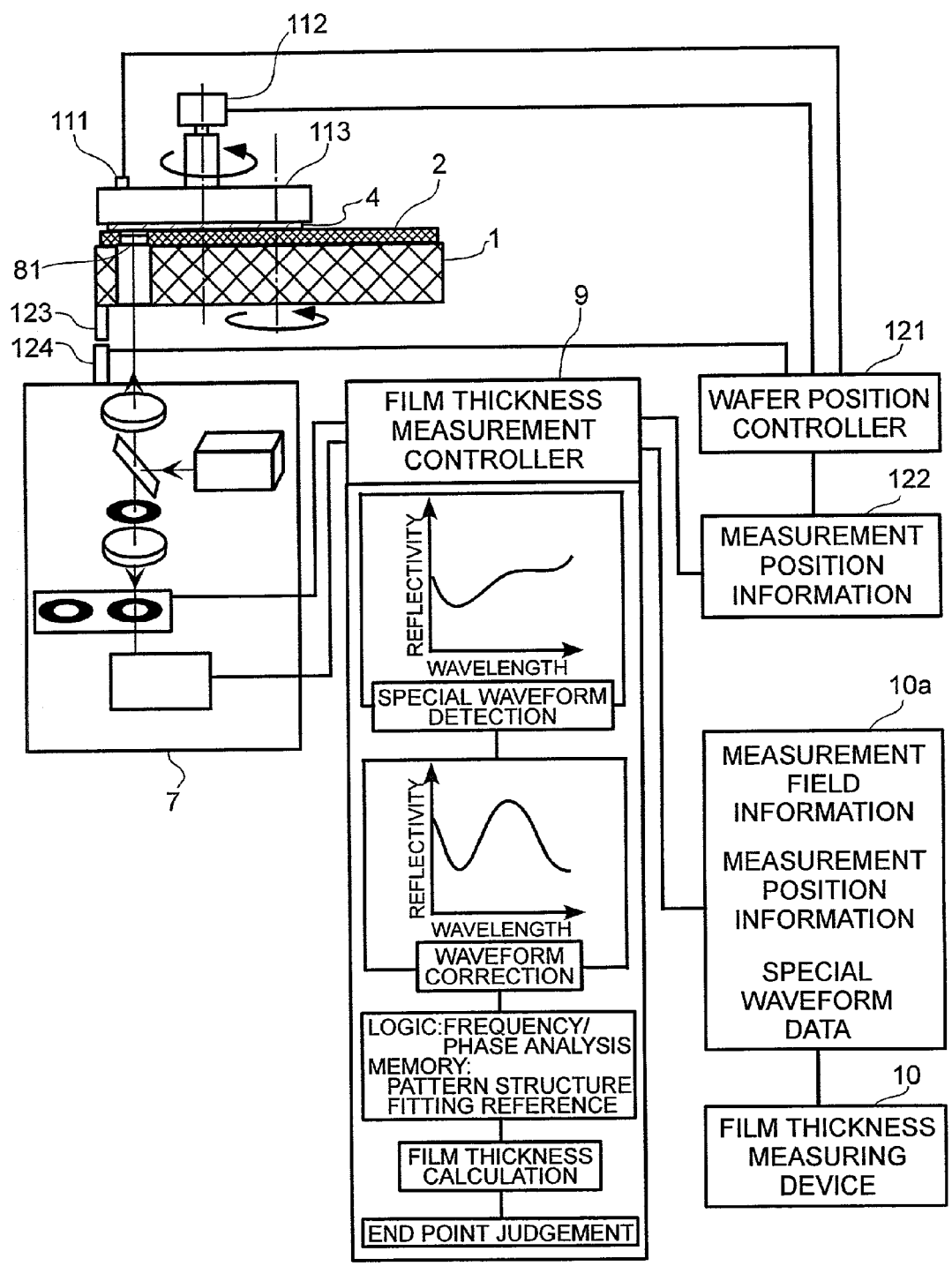
FIG. 13 is a front view showing the general composition of a CMP processing device according to the present invention.

FIG. 12 and FIG. 13 are diagrams for describing a method for controlling the film thickness distribution in a wafer surface by measuring the film thickness distribution for the whole wafer surface during a CMP processing stage.

In FIG. 12 and FIG. 13, description of the composition and actions which are the same as those described in FIG. 2 is omitted here. In FIG. 12, a position sensor 111 and angle of rotation detector 112 are further provided on the holder 113, and a wafer position controller 121 is provided for calculating measurement positions by detecting the respective positional and angular information derived therefrom. Furthermore, a sensor 124 is also provided in the vicinity of the optical axis 120 of the measurement optics system 7, in order to detect the position of the measurement window 81 in the polishing base.

FIG. 12(a) is a diagram illustrating a method for aligning the position of the wafer 4 and the holder 113. A pre-alignment section 117 consisting of a wafer holder 114 capable of holding and rotating the wafer 4, and a notch sensor 115 for detecting a notch in the wafer 4, is disposed beneath the holder 113. In the aforementioned composition, the wafer holder 114 of the pre-alignment section 117 is rotated, the notch 116 in the wafer is detected by the notch sensor 115, and the wafer holder 113 is halted. Next, the position sensor 111 on the holder 113 is positioned directly above a notch 134, for example, such that it maintains a relative position with the notch 116, and the wafer 4 is mounted onto the holding face 113a of the holder 113. The wafer 4 held on the holding face 113a of the holder 113 is then moved over the polishing base 1 of the CMP device, and polishing and levelling of the wafer 4 is started. FIG.

12(b) shows a general front view of a CMP processing device, and FIG. 12(c) shows a partial plan view thereof.

In FIG. 12, the outer size L1 of the wafer 4, the interval L2 between the centre of the polishing base 1 and the measurement light axis 120 of the measurement optics system 7, and the interval L3 between the centre of the polishing base 1 and the holder 113 are fixed values. Since the holder 113 performs a sliding movement, the amount of slide L4 from a central reference point is detected by a slide sensor 118. In this state, the angular position of the rotation detector 112 of the holder 113 is reset and CMP processing commences. When the sensor 124 detects a measurement start indicator 123 and a measurement start signal is detected by the wafer position controller 124, distances L2–L4 on the measurement light axis 120 from the centre of the wafer 4 at the measurement start position 111a, (L2–L4 being determined by calculating the relative position of the measurement centre 120 from the wafer centre, according to the measurement start indicator 123 which has a relative positional relationship with the notch 116 at which the wafer diameter L1 is detected) and the rotational angle θ of the wafer 4 are set, and for each revolution of the polishing base 1, the measurement positions on the wafer are specified for the film thickness on the basis of the spectral waveforms measured by the measurement optics system 7.

Therefore, it is possible to judge whether a chip in the centre or the periphery of the wafer surface illustrated in FIG. 9 is being measured. For example, in the case of CMP processing a wafer of φ 200 mm having SiO2 relative insulation films, then the polishing base will process approximately several nm in one revolution (at approximately 100 rpm), and it will process approximately 200 nm in one minute. Since the accuracy of film thickness measurement according to the present invention enables film thickness variations of the order of several 10 nm to be detected, it is also possible for measurement positions to be identified for each revolution of the polishing base 1, and the remaining film thickness calculated and displayed accordingly.

Figure 14:
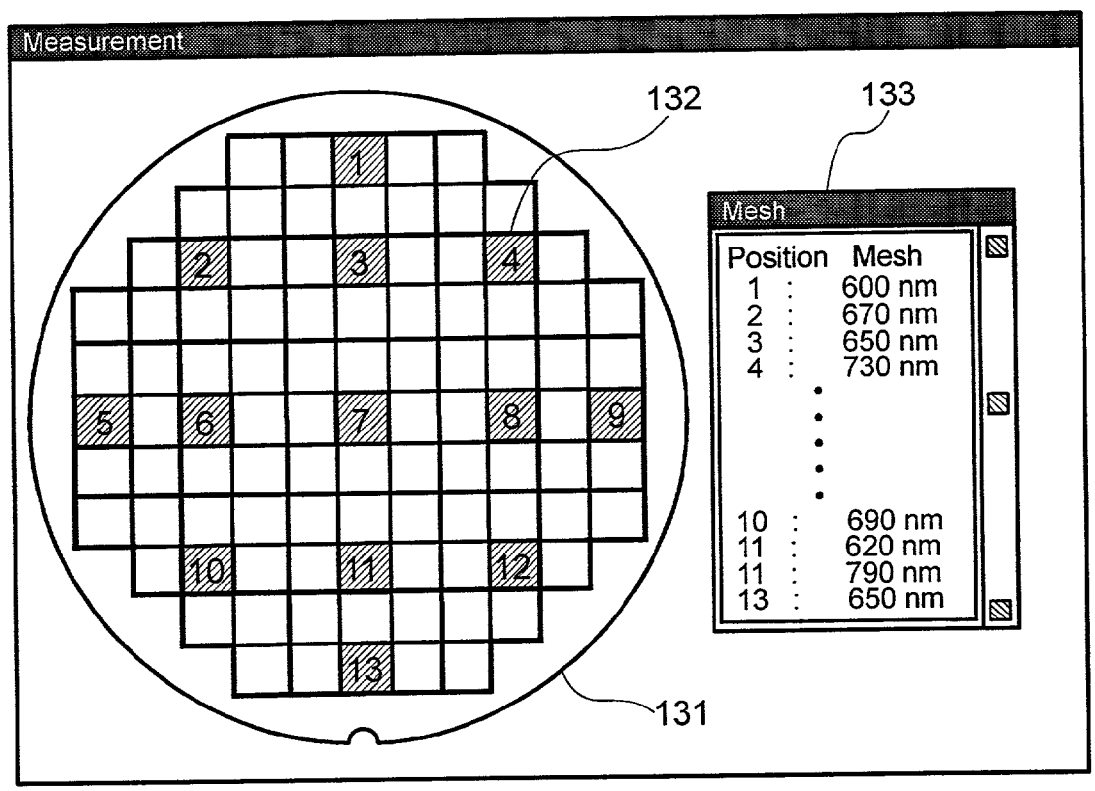
FIG. 14 is a front view of a display screen showing one example of a screen displaying measurement results according to the present invention.
Figure 15:
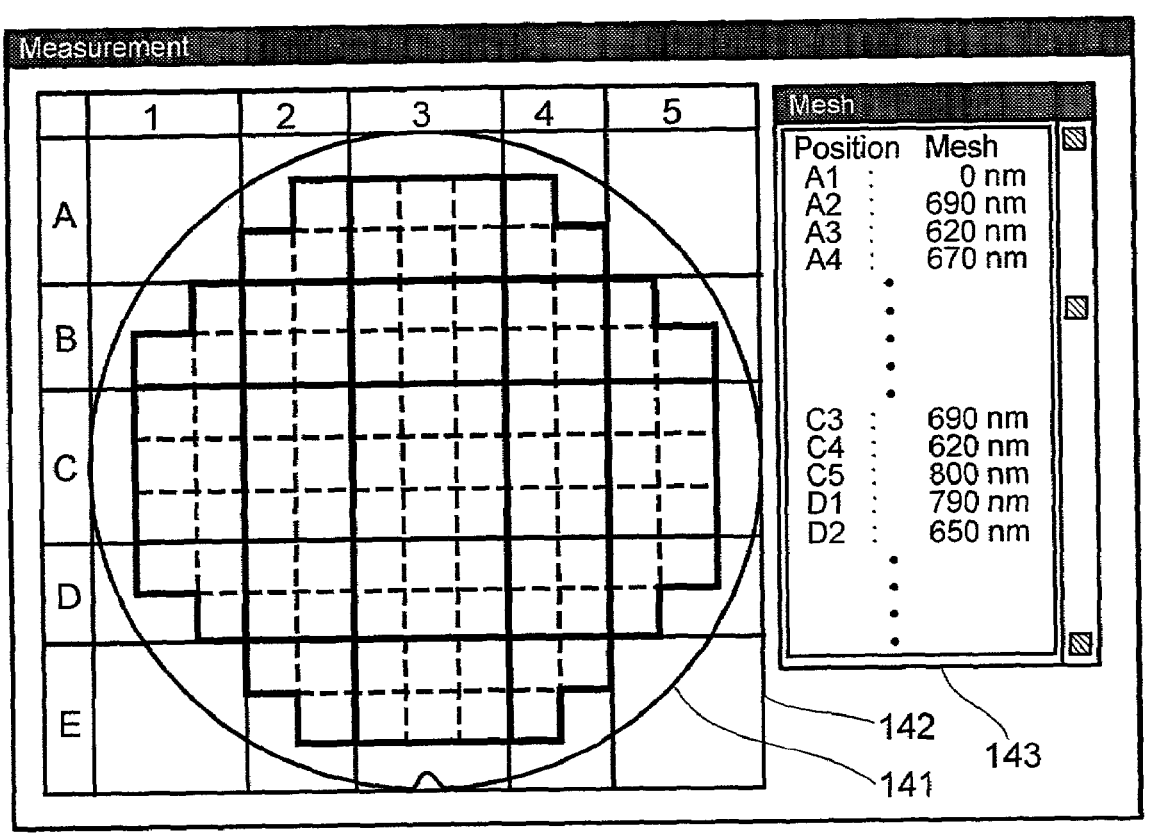
FIG. 15 is a front view of a display screen showing one example of a screen displaying measurement results according to the present invention.

FIG. 14 and FIG. 15 show a state where measurements of the remaining film thickness are displayed. FIG. 14 shows the remaining film thickness for each chip and FIG. 15 shows the remaining film thickness for each region covering a plurality of chips. These results are output in real-time during CMP processing, and the process is terminated when a prescribed remaining film thickness is achieved. The measurement results shown in FIG. 14 and FIG. 15 can be managed as a history for the processed wafer, and by appending these measurement results to the wafer and incorporating same into the processing conditions for subsequent processing, and the like, a benefit is obtained in that throughput and product quality are improved in the manufacturing process.

FIG. 16 is a diagram illustrating a manufacturing method for a semiconductor device according to the present invention. In this manufacturing method for a semiconductor device according to the present invention, a thin film is formed on the surface of a wafer 151 by sputtering, or the like, using a film deposition device 152, whereupon the wafer is conveyed to a CMP processing stage 153. In the CMP processing stage 153, the film thickness is processed to an even thickness by means of a CMP device 154, whilst controlling the film thickness on the surface of the wafer 151 by means of a process end point detecting section 155 implementing a method as described in the aforementioned embodiments, whereupon the processed wafer is washed by a washing device 156, and if necessary, the film thickness at prescribed locations on the wafer 151 is measured by means of a film thickness measuring device 157. This measurement of the film thickness by means of the film thickness measuring device 157 need not necessarily be performed for the whole wafer, but rather, it may also be performed for a selected wafer or number of wafers, according to requirements. The wafer having undergone the CMP processing stage 153 is then formed with wiring patterns, and the like, by passing through an exposure device stage 158, and an etching stage 159, whereupon it is conveyed to subsequent processes.

In the present invention, since the measurement of the film thickness in the CMP processing stage can be carried out during CMP processing, and moreover, since the film thickness can be measured at specified positions on the wafer, it is possible to improve the evenness of the wafer surface after processing, significantly, compared to conventional techniques, by supplying these film thickness measurement results as feedback into the CMP processing conditions, such as the slurry conditions (material, density, supply rate), pad conditions (material, shape, dressing, replacement schedule, and the like), polishing revolution rate, wafer holding pressure, and the like, in the CMP device 154. In this way, a wafer having a surface of significantly improved evenness after CMP processing is obtained, and by subsequent exposure and etching processes, it is possible to form fine patterns having very high reliability.

Moreover, the film thickness measurement results for thickness distribution across the wafer surface can also be appended to the wafer 151 after it has been CMP processed whilst monitoring film thickness as in the present invention. By using these appended measurement results, the etching conditions in the etching process 159 (etching time, applied voltage, gas supply volume, etc.) can be controlled to optimum conditions and hence a semiconductor wafer 160 of very high quality can be manufactured.

According to the present invention, it is possible to perform high-precision film thickness measurement of transparent film in a semiconductor device during polishing by a CMP process, and hence highly accurate control of the polishing process can be achieved on the basis of the measured film thickness data. Furthermore, since the film thickness distribution in the surface of the silicon wafer (substrate) of the semiconductor device being polished can be controlled to a high degree of accuracy, it is possible to optimize the levelling process in the CMP processing stage based on this film thickness distribution, and also to optimize the film deposition conditions in the film deposition stage, and the processing conditions in the etching stage, thereby enabling the manufacture of a high-precision system device. Moreover, the end point for a CMP process in the aforementioned method and production line for manufacturing semiconductor devices on a silicon wafer, can be detected with a high degree of accuracy, and therefore the throughput of the process can be improved.

The invention may be embodied in other specific forms without departing from the spirit or essential characteristics thereof. The present embodiment is therefore to be considered in all respects as illustrative and not restrictive, the scope of the invention being indicated by the appended claim rather than by the foregoing description and all changes which come within the meaning and range of equivalency of the claims are therefore intended to be embraced therein.

What is claimed is:

1. A method for measuring thickness of a thin film, the method comprising:

irradiating white light onto an area of a surface of a sample having an optically transparent thin film thereon, during polishing;

detecting reflected light from said area of said sample due to the irradiation with said white light; and determining the thickness of said optically transparent film on said area by using information from the spectral waveform of the reflected light thus detected;

wherein, in said step of determining the film thickness, the film thickness is determined by using information from the spectral waveform of the reflected light from said area which is selected from said surface by using information from at least one of the spectral waveform, reflectivity of the surface of the sample, and a frequency spectrum in the spectral waveform, on the basis of a characteristic quantity of the spectral waveform of the reflected light from said sample by the irradiation of said white light.

2. The method for measuring the thickness of a thin film according to claim 1, wherein the characteristic quantity of the spectral waveform of said reflected light is based on reflection intensity of the spectral waveform of said reflected light.

3. The method for measuring the thickness of a thin film according to claim 1, wherein the characteristic quantity of the spectral waveform of said reflected light is based on frequency spectrum intensity of the spectral waveform of said detected reflected light.

4. The method for measuring the thickness of a thin film according to claim 1, wherein the characteristic quantity of the spectral waveform of said reflected light is the similarity of the spectral waveform based on a previously measured film thickness distribution.

5. A method for measuring the thickness of a thin film, comprising the steps of:

irradiating white light onto a select area of the surface of a sample whereon an optically transparent thin film is formed, during polishing;

detecting the reflected light reflected from said select area of said sample due to the irradiation of said white light, by time division; and determining the thickness of said optically transparent film at prescribed regions of the surface of said sample, by using information of a characteristic quantity of the spectral waveform of the reflected light thus detected by time divisions, wherein the select area is selected based on information from at least one of the spectral waveform, reflectivity of the surface of the sample with respect to the white light, and a frequency spectrum of the spectral waveform.

6. A method for measuring thickness of a thin film comprising:

irradiating white light onto a surface of a sample having an optically transparent thin film thereon, during polishing;

detecting light reflected from an area of said sample which is selected from said surface by using at least one of a spectral waveform, reflectivity of the surface of the sample with respect to the white light, and a frequency spectrum of the spectral waveform, from the reflected light from said sample by the irradiation of said white light; and determining the thickness of said optically transparent film by using information of a characteristic quantity of the spectral waveform of the reflected light from the prescribed regions thus detected.

7. The method for measuring the thickness of a thin film according to claim 6, wherein the information of a characteristic quantity of the spectral waveform of said reflected light comprises information about the reflection intensity of the spectral waveform of said reflected light.

8. The method for measuring the thickness of a thin film according to claim 6, wherein the information of a characteristic quantity of the spectral waveform of said reflected light comprises information about a frequency spectrum intensity of the spectral waveform of said detected reflected light.

9. The method for measuring the thickness of a thin film according to claim 6, wherein the information of a characteristic quantity of the spectral waveform of said reflected light comprises information about similarity of the spectral waveform based on a previously measured film thickness distribution.

10. A method for measuring the thickness of a thin film, comprising the steps of:

irradiating white light onto a select area of the surface of a sample whereon an optically transparent thin film is formed, during polishing, while supplying an optically transparent fluid on the surface of the sample;

detecting reflected light reflected from said select area of said sample due to the irradiation of said white light; and determining the thickness of said optically transparent film by using information for the spectral waveform of the reflected light thus detected, wherein the select area is selected based on information for at least one of the spectral waveform, reflectivity of the surface of the sample with respect to the white light, and a frequency spectrum of the spectral waveform.

11. The method for measuring the thickness of a thin film according to claim 10, wherein the thickness of said optically transparent film is determined using information for reflection intensity of the spectral waveform of said reflected light.

12. The method for measuring the thickness of a thin film according to claim 10, wherein the thickness of said optically transparent film is determined using information for reflection intensity of the spectral waveform of said reflected light.

13. A method for measuring the thickness of a thin film, comprising the steps of:

irradiating white light onto the a select area of a surface of a sample whereon an optically transparent thin film is formed, during polishing;

detecting the reflected light reflected from said select area of said sample due to the irradiation of said white light, by means of an optical glass having a similar index of refraction to that of the polishing fluid; and determining the thickness of said optically transparent film, on the basis of the spectral waveform of the reflected light thus detected, wherein the select area is selected based on information from at least one of the spectral waveform, reflectivity of the surface of the sample with respect to the white light, and a frequency spectrum of the spectral waveform.

14. The method for measuring the thickness of a thin film according to claim 13, wherein the thickness of said optically transparent film is determined using information for the reflection intensity of the spectral waveform of said reflected light.

15. The method for measuring the thickness of a thin film according to claim 13, wherein the thickness of said optically transparent film is determined using information for the reflection intensity of the spectral waveform of said reflected light.

16. A device for measuring the thickness of a thin film, comprising:
means for irradiating white light onto a select area the surface of a sample whereon an optically transparent thin film is formed, during polishing;
detecting means for detecting the reflected light reflected from said select area of said sample due to the irradiation by said irradiation means;
investigation region setting means for setting regions for determining the thickness of said optically transparent film, by using the information of any one of the spectral waveform of the reflected light detected by said detecting means, the reflectivity of the surface of said sample with respect to said white light, or the information for the frequency spectrum of said spectral waveform; and
film thickness calculating means for calculating the thickness of said optically transparent film by using information for the spectral waveform of the reflected light from the regions set by said investigation region setting means,
wherein the select area is selected based on information from at least one of the spectral waveform, reflectivity of the surface of the sample with respect to the white light, and a frequency spectrum of the spectral waveform.

17. The device for measuring the thickness of a thin film according to claim 16, wherein said film thickness calculating means determines the thickness of said optically transparent film by using information for the reflection intensity in the spectral waveform of said reflected light.

18. The device for measuring the thickness of a thin film according to claim 16, wherein said film thickness calculating means determines the thickness of said optically transparent film by using information for the reflection intensity in the spectral waveform of said reflected light.

19. A device for measuring the thickness of a thin film, comprising:
means for irradiating white light onto a select area of the surface of a sample whereon an optically transparent thin film is formed, during polishing;
detecting means for detecting the reflected light reflected from said select area of said sample due to the irradiation said irradiation means;
investigation region setting means for setting detection regions for determining the thickness of said optically transparent film, on the basis of the spectral waveform of the reflected light detected by said detecting means;
means for extracting a characteristic quantity of the spectral waveform of the reflected light generated by the detection regions on said sample as set by said investigation region setting means; and
film thickness calculating means for calculating means the thickness of said optically transparent film at said detection regions on the basis of said characteristic quantity,
wherein the select area is selected based on information from at least one of the spectral waveform, reflectivity of the surface of the sample with respect to the white light, and a frequency spectrum of the spectral waveform.

20. The device for measuring the thickness of a thin film according to claim 19, wherein said film thickness calculating means determines the thickness of said optically transparent film by using information for the reflection intensity of the spectral waveform of said reflected light.

21. The device for measuring the thickness of a thin film according to claim 19, wherein said film thickness calculating means determines the thickness of said optically transparent film by using information for the reflection intensity of the spectral waveform of said reflected light.

22. A device for measuring the thickness of a thin film, comprising:
means for irradiating white light onto a select area of the surface of a sample whereon an optically transparent thin film is formed, during polishing;
detecting means for detecting the reflected light reflected from said select area of said sample due to the irradiation by said irradiation means;
measurement region setting means for setting regions for determining the thickness of said optically transparent film, on the basis of the spectral waveform of the reflected light detected by said detecting means;
characteristic quantity extracting means for extracting a characteristic quantity of a plurality of spectral waveforms of the reflected light by detecting, by time division, the reflected light from the regions set by said measurement region setting means; and
film thickness calculating means for calculating the thickness of said transparent film, at the regions for determining said film thickness, by using information of the characteristic quantity extracted by said characteristic quantity extracting means,
wherein the select area is selected based on information from at least one of the spectral waveform, reflectivity of the surface of the sample with respect to the white light, and a frequency spectrum of the spectral waveform.

23. The device for measuring the thickness of a thin film according the claim 22, wherein said characteristic quantity extracting means extracts information for the reflection intensity of a plurality of spectral waveforms of said reflected light, as the characteristic quantity for the plurality of spectral waveforms of the reflected light.

24. The device for measuring the thickness of a thin film according to claim 22, wherein said characteristic quantity extracting means extracts information for the frequency spectrum intensity of a plurality of spectral waveforms of said reflected light, as the characteristic quantity for the plurality of spectral waveforms of the reflected light.

* * * * *